(12) United States Patent
Park et al.

(10) Patent No.: US 12,334,222 B2
(45) Date of Patent: Jun. 17, 2025

(54) ARTIFICIAL INTELLIGENCE-BASED SCALP IMAGE DIAGNOSTIC ANALYSIS SYSTEM USING BIG DATA, AND PRODUCT RECOMMENDATION SYSTEM USING THE SAME

(71) Applicant: ARAMHUVIS CO., LTD., Gyeonggi-do (KR)

(72) Inventors: Dong Soon Park, Mungyeong-si (KR); Jeong Il Jeong, Seoul (KR)

(73) Assignee: ARAM HUVIS CO., LTD., Seongnam-si (KR)

( * ) Notice: Subject to any disclaimer, the term of this patent is extended or adjusted under 35 U.S.C. 154(b) by 187 days.

(21) Appl. No.: 17/765,281

(22) PCT Filed: Jul. 12, 2021

(86) PCT No.: PCT/KR2021/008868
§ 371 (c)(1),
(2) Date: Mar. 30, 2022

(87) PCT Pub. No.: WO2022/030782
PCT Pub. Date: Feb. 10, 2022

(65) Prior Publication Data
US 2023/0178238 A1    Jun. 8, 2023

(30) Foreign Application Priority Data
Aug. 3, 2020   (KR) .......................... 10-2020-0096968

(51) Int. Cl.
*G06T 7/00*        (2017.01)
*G06V 10/82*      (2022.01)
(Continued)

(52) U.S. Cl.
CPC .......... *G16H 50/20* (2018.01); *G06T 7/0012* (2013.01); *G06V 10/82* (2022.01); *G16H 30/20* (2018.01);
(Continued)

(58) Field of Classification Search
CPC ........ G06T 7/0012; G06T 2207/20081; G06V 10/82
See application file for complete search history.

(56) References Cited

U.S. PATENT DOCUMENTS

2016/0253799 A1* 9/2016 Rahman ................... G06T 5/70
                                                                    382/128
2021/0366614 A1* 11/2021 Chee Chong ........ A61B 5/7475

FOREIGN PATENT DOCUMENTS

JP      2018-097899 A     6/2018
KR   10-2015-0025830 A     3/2015
(Continued)

*Primary Examiner* — Ayodeji O Ayotunde
(74) *Attorney, Agent, or Firm* — PARK LAW FIRM

(57) ABSTRACT

Proposed is an artificial intelligence-based scalp image diagnostic analysis system, and a product recommendation system using the same, which can achieve an accurate diagnosis function through an artificial intelligence (deep learning) image analysis using a scalp image measured by a diagnostician, with which a diagnosis result can be confirmed in real time, enabling a high-accuracy diagnosis result to be obtained, and which can recommend a product that is suitable for the state of the scalp according to the diagnosis result diagnosed by means of artificial intelligence.

6 Claims, 13 Drawing Sheets

(51) Int. Cl.
  *G16H 30/20*   (2018.01)
  *G16H 50/20*   (2018.01)
  *G16H 50/70*   (2018.01)

(52) U.S. Cl.
  CPC ... *G16H 50/70* (2018.01); *G06T 2207/20081* (2013.01)

(56) References Cited

FOREIGN PATENT DOCUMENTS

| | | |
|---|---|---|
| KR | 10-2019-0071911 A | 6/2019 |
| KR | 10-2020-0081885 A | 7/2020 |
| WO | 2018-140014 A1 | 8/2018 |

* cited by examiner

FIG. 7

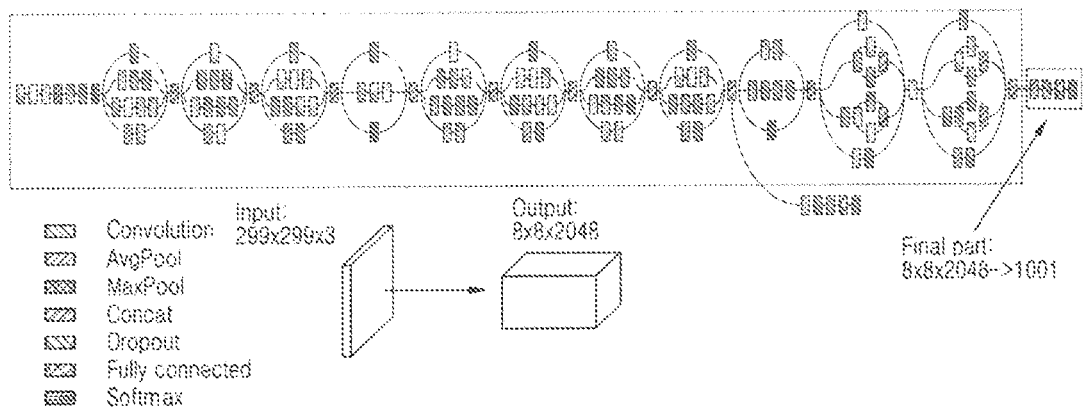

FIG. 8a

Scalp diagnosis AI labelling (dry, oily, sensitive, scurfy, folliculitis)

| Select file | No file selected | Start AI analysis |

Dry scalp learning data : 2,709 images (+ 938 images)
Oily scalp learning data : 592 images (+ 81 images)
Sensitive scalp learning data : 782 images (+ 37 images)
Folliculitis scalp learning data : 187 images (+ 2 images)
Scurfy scalp learning data : 293 images (+ 84 images)
Learning data of scurfy image detection : 86 images)
Comparison target data having good scalp : 805 images

FIG. 8b

Scalp diagnosis AI labelling (dry, oily, sensitive, scurfy, folliculitis)

Dry scalp learning data : 2,709 data (+ 938 data)
Oily scalp learning data : 592 data (+ 81 data)
Sensitive scalp learning data : 782 data (+ 37 data)
Folliculitis scalp learning data : 187 data (+ 2 data)
Scurfy scalp learning data : 293 data (+ 84 data)
Learning data of scurfy image detection : 86 data)
Comparison target data having good scalp : 805 data

FIG. 9

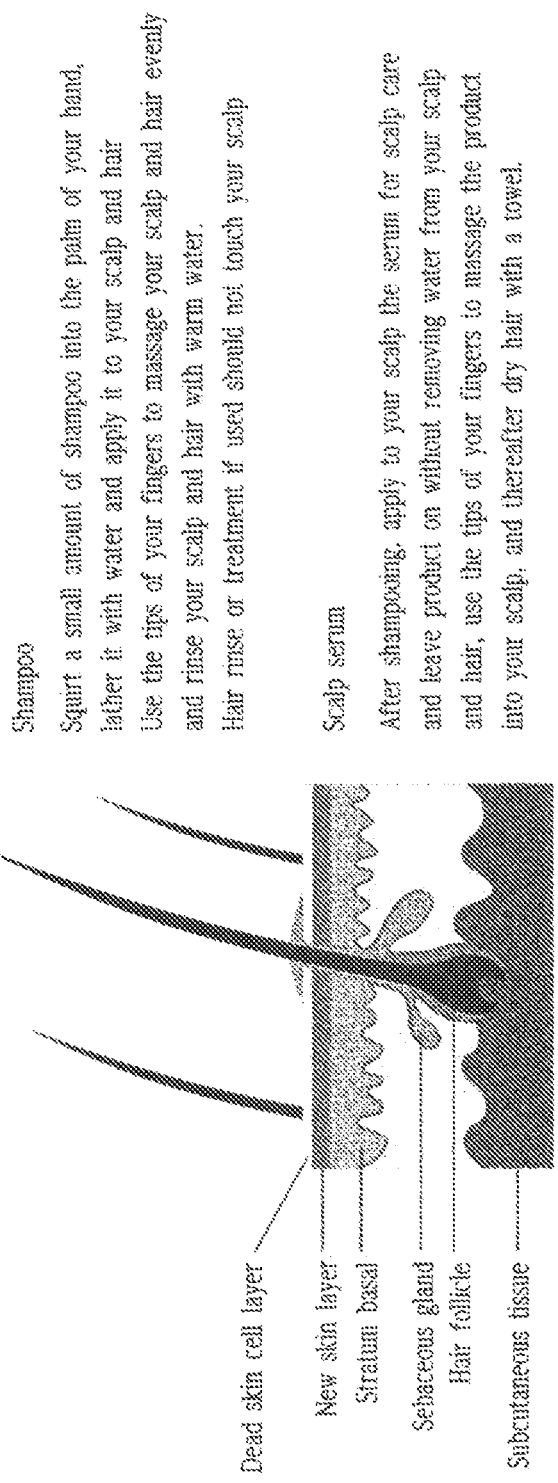

Dead skin cell layer
New skin layer
Stratum basal
Sebaceous gland
Hair follicle
Subcutaneous tissue Shampoo
Squirt a small amount of shampoo into the palm of your hand, lather it with water and apply it to your scalp and hair
Use the tips of your fingers to massage your scalp and hair evenly and rinse your scalp and hair with warm water.
Hair rinse or treatment if used should not touch your scalp Scalp serum
After shampoing, apply to your scalp the serum for scalp care and leave product on without removing water from your scalp and hair, use the tips of your fingers to massage the product into your scalp, and thereafter dry hair with a towel.

FIG. 10

| Diagnostic Value for Dead Skin Cell Amount | Scalp Type | Detailed Scalp Type | Diagnostic Value for Pore Status | Determination of Detailed Scalp Type |
|---|---|---|---|---|
| ★★★★★ | A. Itchy and oily scalp | A-1. Scalp having active secretion of sebum | ★☆☆☆☆ | A-3.Seborrhoeic scalp |
| | | | ★★☆☆☆ | A-2.Scalp having active secretion of sebum and accompanying inflammation |
| | | | ★★★☆☆ | A-1.Scalp having active secretion of sebum |
| | B. Dry and flaky scalp | B-1. Dry scalp | ★☆☆☆☆ | B-3.Atopic scalp |
| | | | ★★☆☆☆ | B-2.Dry scalp having dead skin cells flying like powder |
| | | | ★★★☆☆ | B-1.Dry scalp |
| | C. Troubled (eruption, etc.) scalp | C-1. Scalp soothing and post-treatment | ★☆☆☆☆ | C-2.Papular and pustular due to folliculitis |
| | | | ★★☆☆☆ | C-1.Scalp soothing and post-treatment |
| ★★★★☆ | A. Itchy and oily scalp | A-1. Scalp having active secretion of sebum | ★☆☆☆☆ | A-3.Seborrhoeic scalp |
| | | | ★★☆☆☆ | A-2.Scalp having active secretion of sebum and accompanying inflammation |
| | | | ★★★☆☆ | A-1.Scalp having active secretion of sebum |
| | B. Dry and flaky scalp | B-1. Dry scalp | ★☆☆☆☆ | B-3.Atopic scalp |
| | | | ★★☆☆☆ | B-2.Dry scalp having dead skin cells flying like powder |
| | | | ★★★☆☆ | B-1.Dry scalp |
| | C. Troubled (eruption, etc.) scalp | C-1. Scalp soothing and post-treatment | ★☆☆☆☆ | C-2.Papular and pustular due to folliculitis |
| | | | ★★☆☆☆ | C-1.Scalp soothing and post-treatment |
| ★★★☆☆ | A. Itchy and oily scalp | A-1. Scalp having active secretion of sebum | ★☆☆☆☆ | A-3.Seborrhoeic scalp |
| | | | ★★☆☆☆ | A-2.Scalp having active secretion of sebum and accompanying inflammation |
| | | | ★★★☆☆ | A-1.Scalp having active secretion of sebum |
| | B. Dry and flaky scalp | B-1. Dry scalp | ★☆☆☆☆ | B-3.Atopic scalp |
| | | | ★★☆☆☆ | B-2.Dry scalp having dead skin cells flying like powder |
| | | | ★★★☆☆ | B-1.Dry scalp |
| | C. Troubled (eruption, etc.) scalp | C-1. Scalp soothing and post-treatment | ★☆☆☆☆ | C-2.Papular and pustular due to folliculitis |
| | | | ★★☆☆☆ | C-1.Scalp soothing and post-treatment |
| ★★☆☆☆ | A. Itchy and oily scalp | A-2. Scalp having active secretion of sebum and accompanying inflammation | ★☆☆☆☆ | A-3.Seborrhoeic scalp |
| | | | ★★☆☆☆ | A-2.Scalp having active secretion of sebum and accompanying inflammation |
| | B. Dry and flaky scalp | B-2. Dry and flaky scalp | ★☆☆☆☆ | B-3.Atopic scalp |
| | | | ★★☆☆☆ | B-2.Dry scalp having dead skin cells flying like powder |
| | C. Troubled (eruption, etc.) scalp | C-1. Scalp soothing and post-treatment | ★☆☆☆☆ | C-2.Papular and pustular due to folliculitis |
| | | | ★★☆☆☆ | C-1.Scalp soothing and post-treatment |
| ★☆☆☆☆ | A. Itchy and oily scalp | A-3. Seborrhoeic scalp | ★☆☆☆☆ | A-3.Seborrhoeic scalp |
| | | | ★★☆☆☆ | A-3.Seborrhoeic scalp |
| | B. Dry and flaky scalp | B-3. Atopic scalp | ★☆☆☆☆ | B-3.Atopic scalp |
| | | | ★★☆☆☆ | B-3.Atopic scalp |
| | C. Troubled (eruption, etc.) scalp | C-2. Papular and pustular due to folliculitis | ★☆☆☆☆ | C-2.Papular and pustular due to folliculitis |
| | | | ★★☆☆☆ | C-2.Papular and pustular due to folliculitis |

FIG. 11

| Diagnostic Value for Dead Skin Cell Amount | Scalp Type | Detailed Scalp Type | Pore Status | Determination of Scalp Type | Shampoo | Serum |
|---|---|---|---|---|---|---|
| ★★★★★ | A. Itchy and oily scalp | A-1. Scalp having active secretion of sebum | ★☆☆☆☆ | A-3 | A-3 | S-3 |
| | | | ★★☆☆☆ | A-2 | A-2 | S-2 |
| | | | ★★★☆☆ | A-1 | A-1 | S-1 |
| | B. Dry and flaky scalp | B-1. Dry scalp | ★☆☆☆☆ | B-3 | B-3 | S-6 |
| | | | ★★☆☆☆ | B-2 | B-2 | S-5 |
| | | | ★★★☆☆ | B-1 | B-1 | S-4 |
| | C. Troubled (eruption, etc.) scalp | C-1. Scalp soothing and post-treatment | ★☆☆☆☆ | C-2 | C-2 | S-8 |
| | | | ★★☆☆☆ | C-1 | C-1 | S-7 |
| ★★★★☆ | A. Itchy and oily scalp | A-1. Scalp having active secretion of sebum | ★☆☆☆☆ | A-3 | A-3 | S-3 |
| | | | ★★☆☆☆ | A-2 | A-2 | S-2 |
| | | | ★★★☆☆ | A-1 | A-1 | S-1 |
| | B. Dry and flaky scalp | B-1. Dry scalp | ★☆☆☆☆ | B-3 | B-3 | S-6 |
| | | | ★★☆☆☆ | B-2 | B-2 | S-5 |
| | | | ★★★☆☆ | B-1 | B-1 | S-4 |
| | C. Troubled (eruption, etc.) scalp | C-1. Scalp soothing and post-treatment | ★☆☆☆☆ | C-2 | C-2 | S-8 |
| | | | ★★☆☆☆ | C-1 | C-1 | S-7 |
| ★★★☆☆ | A. Itchy and oily scalp | A-1. Scalp having active secretion of sebum | ★☆☆☆☆ | A-3 | A-3 | S-3 |
| | | | ★★☆☆☆ | A-2 | A-2 | S-2 |
| | | | ★★★☆☆ | A-1 | A-1 | S-1 |
| | B. Dry and flaky scalp | B-1. Dry scalp | ★☆☆☆☆ | B-3 | B-3 | S-6 |
| | | | ★★☆☆☆ | B-2 | B-2 | S-5 |
| | | | ★★★☆☆ | B-1 | B-1 | S-4 |
| | C. Troubled (eruption, etc.) scalp | C-1. Scalp soothing and post-treatment | ★☆☆☆☆ | C-2 | C-2 | S-8 |
| | | | ★★☆☆☆ | C-1 | C-1 | S-7 |
| ★★☆☆☆ | A. Itchy and oily scalp | A-2. Scalp having active secretion of sebum and accompanying inflammation | ★☆☆☆☆ | A-3 | A-3 | S-4 |
| | | | ★★☆☆☆ | A-2 | A-2 | S-3 |
| | B. Dry and flaky scalp | B-2. Dry and flaky scalp | ★☆☆☆☆ | B-3 | B-3 | S-6 |
| | | | ★★☆☆☆ | B-2 | B-2 | S-6 |
| | C. Troubled (eruption, etc.) scalp | C-1. Scalp soothing and post-treatment | ★☆☆☆☆ | C-2 | C-2 | S-9 |
| | | | ★★☆☆☆ | C-1 | C-1 | S-8 |
| ★☆☆☆☆ | A. Itchy and oily scalp | A-3. Seborrheic scalp | ★☆☆☆☆ | A-3 | A-3 | S-3 |
| | | | ★★☆☆☆ | A-3 | A-3 | S-3 |
| | B. Dry and flaky scalp | B-3. Atopic scalp | ★☆☆☆☆ | B-3 | B-3 | S-4 |
| | | | ★★☆☆☆ | B-3 | B-3 | S-4 |
| | C. Troubled (eruption, etc.) scalp | C-2. Papular and pustular due to folliculitis | ★☆☆☆☆ | C-2 | C-2 | S-9 |
| | | | ★★☆☆☆ | C-2 | C-2 | S-9 |

FIG. 12

Example of product recommendation for itchy and oily scalp type

| | Scalp typea A-1 | Scalp typea A-2 | Scalp typea A-3 |
|---|---|---|---|
| Product | Itchy and oily scalp | Itchy and oily scalp | Itchy and oily scalp |
| | Scalp having active secretion of sebum | Scalp having active secretion of sebum and accompanying inflammation | Seborrhoeic scalp |
| Shampoo | A-1 | A-2 | A-3 |
| | - Strong detergency and rich bubbles (Amino-based anionic surfactant) Scalp stimulation minimized | - Strong detergency and rich bubbles (Amino-based anionic surfactant) Anti-inflammatory function added and scalp stimulation minimized | - Excellent detergency Antifungal function added Anti-inflammatory function added |
| Serum | S-1 | S-2 | S-3 |
| | - Scalp stimulation minimized<br>- Secretion of scalp sebum normalized<br>- Itching of the scalp relieved | - Scalp stimulation minimized<br>- Secretion of scalp sebum normalized<br>- Itching of the scalp relieved<br>- Anti-inflammation effect | - Antifungal effect<br>- Scalp stimulation minimized<br>- Itching of the scalp relieved |

ARTIFICIAL INTELLIGENCE-BASED SCALP IMAGE DIAGNOSTIC ANALYSIS SYSTEM USING BIG DATA, AND PRODUCT RECOMMENDATION SYSTEM USING THE SAME

TECHNICAL FIELD

The present disclosure relates generally to an artificial intelligence-based scalp image diagnostic analysis system using big data, and a product recommendation system using the same and, more particularly, to an artificial intelligence-based scalp image diagnostic analysis system using big data, and a product recommendation system using the same, which can achieve an accurate diagnosis function through an artificial intelligence (deep learning) image analysis using a scalp image measured by a diagnostician, and which can recommend a product that is suitable for the state of a customer's scalp according to the diagnosis result diagnosed by means of artificial intelligence.

BACKGROUND ART

Conventionally, a diagnostician compares a reference image by each item with a diagnosis image by the naked eye, searches for similar images, and manually selects a diagnosis value, as shown in FIGS. 1 and 2.

That is, after a diagnostician measures a customer's scalp in images by use of a diagnosis device, the diagnostician should separately confirm a diagnosis result for each diagnosis item (e.g., dry, sensitive, inflammatory, with hair loss, good, oily, scurfy, and seborrhoeic) later; that is, confirmation in real time is not available. Accordingly, the diagnostician cannot obtain the diagnosis result (e.g., "inflammatory" among several items) until before the analysis and diagnosis result with respect to measurement data about the customer's scalp is input after a professional compares the images by the naked eye.

The conventional art as described above has a problem such that the rate of obtaining the diagnosis result is slow and the accuracy of the diagnosis result is low (less than 70%).

DISCLOSURE

Technical Problem

Accordingly, the present disclosure has been made keeping in mind the above problem occurring in the related art, and an objective of the present disclosure is to provide an artificial intelligence-based scalp image diagnostic analysis system using big data, and a product recommendation system using the same, which can achieve an accurate diagnosis function through an artificial intelligence (deep learning) image analysis using a scalp image measured by a diagnostician, with which a diagnosis result can be confirmed in real time, enabling a high-accuracy diagnosis result to be obtained, and which can recommend a product that is suitable for the state of the scalp according to the diagnosis result diagnosed by means of artificial intelligence.

Technical Solution

In order to accomplish the above objectives, a first exemplary embodiment of the present disclosure provides an artificial intelligence-based scalp image diagnostic analysis system using big data, the system including: a main processor configured to: receive, from a diagnostician, information about a customer's history taken by the diagnostician by asking the customer about his/her history, and a scalp image obtained by any one of a scalp diagnosis device and a terminal, through API(RESTful) as a cloud service; conduct a diagnosis by a self-diagnosis algorithm with respect to the received history-taking information; and transmit the received scalp image to an artificial-intelligence processor which performs a scalp analysis;

the artificial-intelligence processor configured to perform an artificial intelligence (AI) analysis and recommendation service to label the scalp image received from the main processor with all or some of diagnosis items (e.g., dry, sensitive, inflammatory, with hair loss, good, oily, scurfy, and seborrhoeic) by use of data accumulated in database;

a scalp diagnosis AI algorithm configured to: receive, from the artificial-intelligence processor, information labeled with all or some of the diagnosis items; conduct a specific precision diagnosis by performing learning and interpretation by a deep learning algorithm; and derive a final diagnosis result; and the database accumulating therein scalp measurement, diagnosis, and recommendation data, which are provided to the main processor, thereby enabling a self-scalp analysis and recommendation to be performed.

A second exemplary embodiment of the present disclosure to accomplish the above objectives provides an artificial intelligence-based scalp image diagnostic analysis system using big data, the system including: a main processor configured to: receive, from a diagnostician, information about a customer's history taken by the diagnostician by asking about the customer's history, and a scalp image obtained by any one of a scalp diagnosis device and a terminal, through API(RESTful) as a cloud service; conduct a diagnosis by a self-diagnosis algorithm with respect to the received history-taking information; label the received scalp image with all or some of diagnosis items (e.g., dry, sensitive, inflammatory, with hair loss, good, oily, scurfy, and seborrhoeic) through an artificial intelligence (AI) analysis by an artificial-intelligence processor using information of big data accumulated in database; extract a precision diagnosis from the labelled information by a scalp diagnosis AI algorithm; and transmit a diagnosis result therefrom and a diagnosis based on the history-taking information in real time back to a terminal of the diagnostician through the API, together with a recommended product customized by suitable prescription;

the artificial-intelligence processor configured to perform an AI analysis to label the scalp image received from the main processor with all or some of diagnosis items (e.g., dry, sensitive, inflammatory, with hair loss, good, oily, scurfy, and seborrhoeic) by use of data accumulated in database;

a scalp diagnosis AI algorithm configured to: receive, from the artificial-intelligence processor, information labeled with all or some of the diagnosis items (e.g., dry, sensitive, inflammatory, with hair loss, good, oily, scurfy, and seborrhoeic); and conduct a specific precision diagnosis by a deep learning algorithm, and derive a final diagnosis result; and the database accumulating therein scalp measurement, diagnosis, and recommendation data, which are provided to the main processor, thereby enabling training and interpretation to be performed.

A third exemplary embodiment of the present disclosure to accomplish the above objectives provides an artificial intelligence-based scalp image diagnostic analysis system using big data, the system including: an artificial-intelligence processor configured to: receive, from a diagnostician, a scalp image obtained by any one of a scalp diagnosis device and a terminal, through API(RESTful) as a cloud service; and performs an artificial intelligence analysis with respect to the received history-taking information to label the received information with all or some of diagnosis items; and
  a scalp diagnosis AI algorithm configured to: receive, from the artificial-intelligence processor, information labeled with all or some of the diagnosis items; conduct a specific precision diagnosis by performing learning and interpretation by use of information of big data by a deep learning algorithm; and derive a final diagnosis result.

Advantageous Effects

According to an artificial intelligence-based scalp image diagnostic analysis system using big data, and a product recommendation system using the same, an accurate diagnosis function through an artificial intelligence (deep learning) image analysis using a scalp image measured by a diagnostician can be achieved, with which a diagnosis result can be confirmed in real time, enabling a high-accuracy diagnosis result to be obtained, and a product that is suitable for the state of the scalp according to the diagnosis result diagnosed by means of artificial to intelligence can be recommended.

DESCRIPTION OF DRAWINGS

FIG. 7 is an exemplary diagram showing an Inception V3 model as a deep learning algorithm in an artificial intelligence-based scalp image diagnostic analysis system using big data and a product recommendation system using the same, according to the present disclosure.

FIGS. 8a to 8c are exemplary views showing that a scalp diagnosis by a diagnostician can be accurately conducted through history taking about a customer's scalp and a scalp image analysis, and a diagnosis result can be promptly obtained in real time, in an artificial intelligence-based scalp image diagnostic analysis system using big data and a product recommendation system using the same, according to the present disclosure.

FIG. 9 is an exemplary view showing product recommendation on the basis of a scalp diagnosis result, which may be a shampoo and scalp serum, product division and algorithm, in an artificial intelligence-based scalp image diagnostic analysis system using big data and a product recommendation system using the same, according to the present disclosure.

FIG. 10 shows the first determination of scalp type according to history taking by a user, the second determination of divided scalp type through a diagnosis by a scalp image artificial intelligence analysis, and algorithm/system, in an artificial intelligence-based scalp image diagnostic analysis system using big data and a product recommendation system using the same, according to the present disclosure.

FIG. 11 shows mapping algorithm and system determined for scalp care shampoo and serum products customized according to the determination of scalp type through the diagnosis by the scalp image artificial-intelligence analysis, in an artificial intelligence-based scalp image diagnostic analysis system using big data and a product recommendation system using the same, according to the present disclosure.

FIG. 12 shows an algorithm and a system for product recommendation by defining customized scalp care shampoo and serum respectively through division of recommended products according to the result of a scalp artificial intelligence diagnosis by a diagnostician, in an artificial intelligence-based scalp image diagnostic analysis system using big data and a product recommendation system using the same, according to the present disclosure.

BEST MODE

Figure 1:
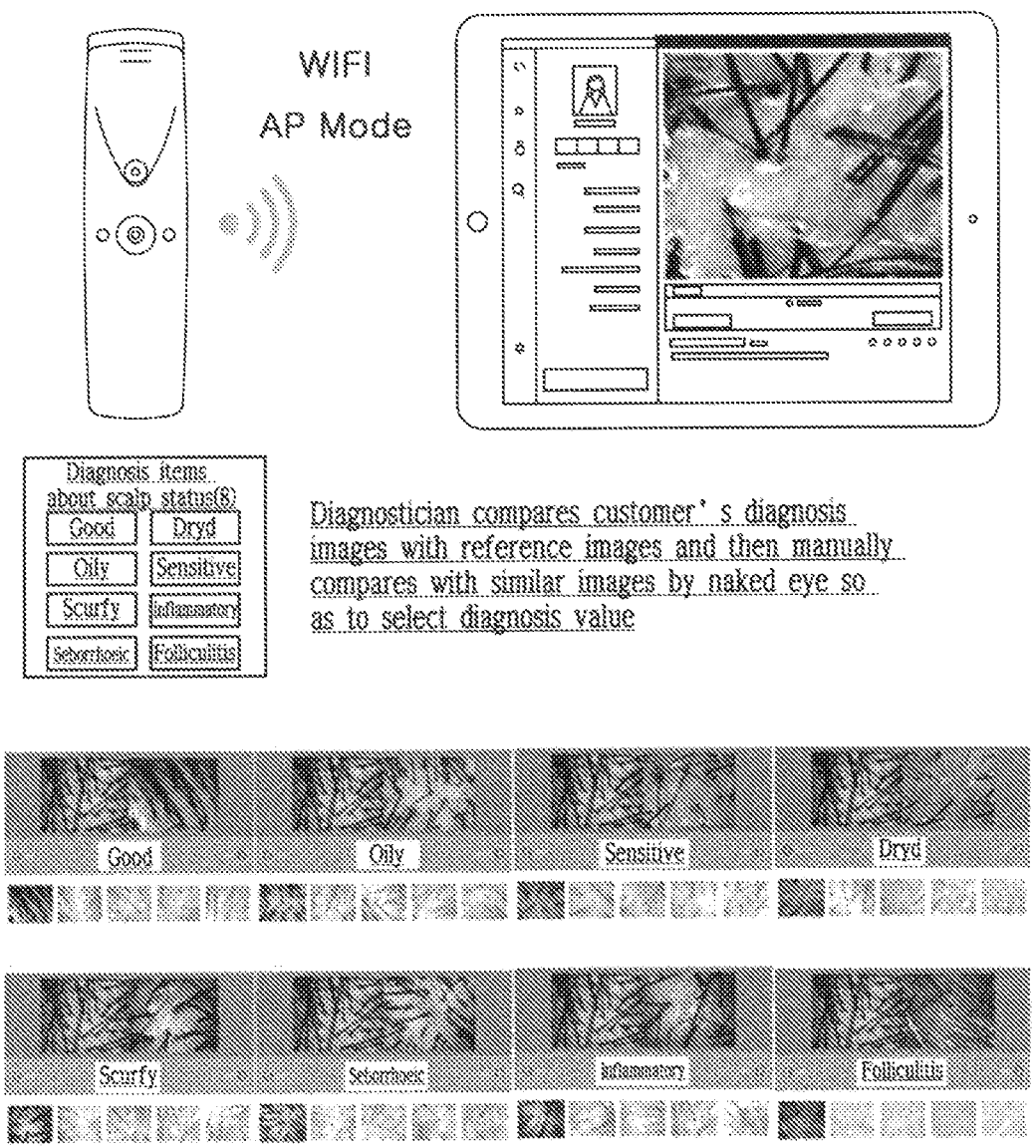
FIGS. 1 and 2 are views showing a method of manually diagnosing the scalp by the naked eye according to the related art.
Figure 2:
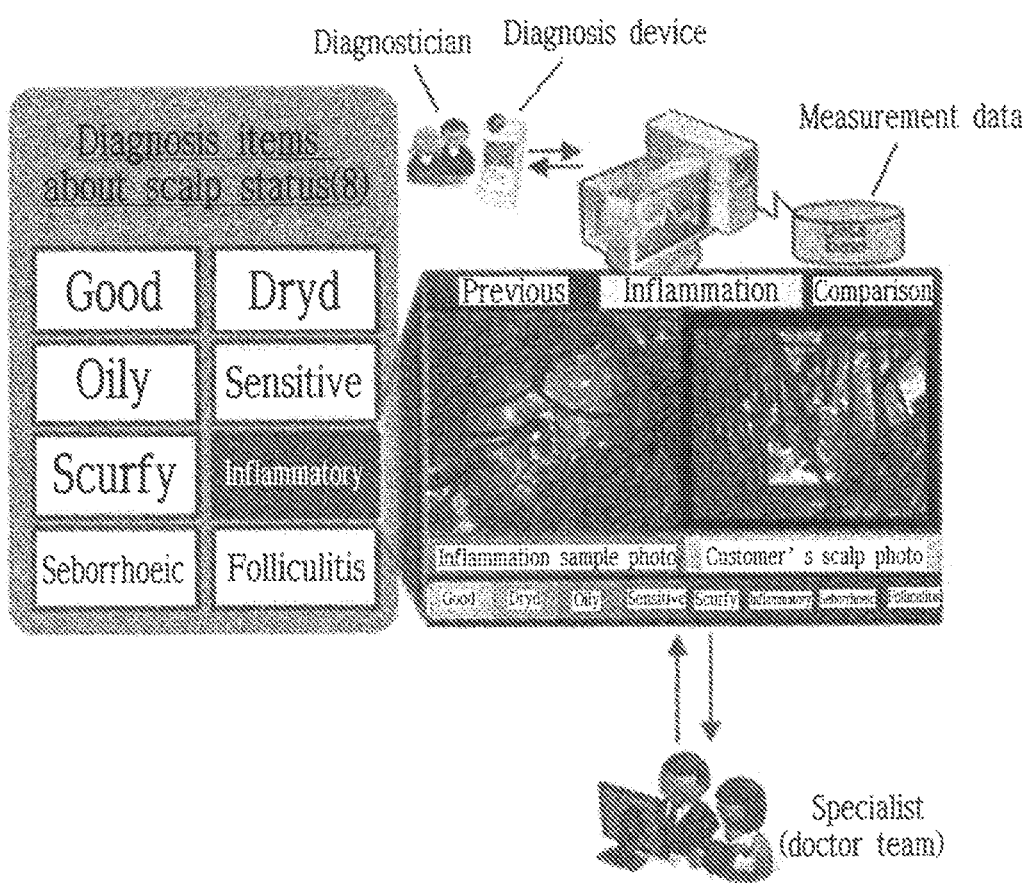

Hereinbelow, exemplary embodiments of the present disclosure will be described in detail with reference to the accompanying drawings.

Exemplary embodiments of an artificial intelligence-based scalp image diagnostic analysis system using big data, and a product recommendation system using the same, according to the present disclosure, will be described with reference to FIGS. 3 and 4, and also with reference to any other accompanying drawings as necessary.

The first exemplary embodiment of the present disclosure is comprised of: a main processor (3) configured to receive, from a diagnostician, information about a customer's history taken by the diagnostician by asking about the customer's history, and a scalp image obtained by any one of a scalp diagnosis device and a terminal (1), through API(RESTful) (2) as a cloud service, conduct a diagnosis by a self-diagnosis algorithm with respect to the received history-taking information, and transmit the received scalp image to an artificial-intelligence processor, for performing a scalp diagnosis; the artificial-intelligence processor (5) configured to perform an AI analysis to label the scalp image received from the main processor (3) with all or some of diagnosis items (e.g., dry, sensitive, inflammatory, with hair loss, good, oily, scurfy, and seborrhoeic) by use of data accumulated in database (4); a scalp diagnosis AI algorithm (6) configured to receive, from the artificial-intelligence processor (5), information labeled with all or some of the diagnosis items (e.g., dry, sensitive, inflammatory, with hair loss, good, oily, scurfy, and seborrhoeic); conduct a specific precision diagnosis by performing and interpretation by deep learning algorithm, and derive a final result analysis; and the database (4) accumulating therein scalp measurement, diagnosis and recommendation data, which are provided to the main processor, to thereby enable self-scalp analysis and recommendation service to be performed, With respect to the history-taking information and the scalp image received from the diagnostician, the main processor (3) diagnoses the history-taking information by a self-diagnosis algorithm constructed in the main processor (3). That is, the history-taking information received from the diagnostician is diagnosed by the self-diagnosis algorithm by being provided with scalp information-associated data accumulated in the database.

The scalp image is labelled with all or some of dry, sensitive, inflammatory, with hair loss, folliculitis, good, oily, scurfy, and seborrheic scalp by the artificial intelligence (AI) analysis, an accurate analysis is extracted from the labelled information by the scalp diagnosis AI algorithm, and the diagnosis result therefrom, and a diagnosis on the basis of the history-taking information is transmitted back to the diagnostician's terminal in real time through API together with a recommended product as a suitable prescription.

The artificial intelligence processor (5) learns about the scalp with respect to the received scalp image by utilizing information of big data as a deep learning stage and collects data, and labels the collected learning data, conducts learning and verification to label the collected data with learning data and test data (8:2), and derives an inference model (CNN: Convolutional Neural Network).

The scalp diagnosis algorithm (6) receives, from the artificial-intelligence processor (5), information labelled with all or some of the diagnosis items such as dry, sensitive, inflammatory, with hair loss, good, oily, scurfy, and seborrhoeic, conducts learning and interpretation with respect to the received labelling information by using information of the big data in the database and the Inception V3 model (refer to FIG. 7) as a deep learning algorithm, and infers an image by additionally retraining a scalp image set, thereby deriving a final diagnosis result with a specific precision diagnosis.

According to the second exemplary embodiment of the present disclosure, the main processor (3) is configured to receive, from a diagnostician, information about a customer's history taken by the diagnostician by asking about the customer's history, and a scalp image obtained by any one of a scalp diagnosis device and a terminal, through API (RESTful) (2) as a cloud service, conduct a diagnosis by a self-diagnosis algorithm with respect to the received history-taking information, label the received scalp image with all or some of the diagnosis items (e.g., dry, sensitive, inflammatory, with hair loss, good, oily, scurfy, and seborrhoeic), through an artificial intelligence analysis by the artificial-intelligence processor using information of big data accumulated in the database, extract a precision diagnosis by the scalp analysis AI algorithm from the labelled information, and transmit a diagnosis result thereof and a diagnosis based on the history-taking information in real time back to the diagnostician's terminal through the API, together with a recommended product customized by the suitable prescription.

The artificial-intelligence processor (5) is configured to perform an AI analysis and recommendation service to label the scalp image received from the main processor (3) with all or some of diagnosis items (e.g., dry, sensitive, inflammatory, with hair loss, good, oily, scurfy, and seborrhoeic) by use of data accumulated in the database (4).

The scalp diagnosis AI algorithm (6) is configured to receive, from the artificial intelligence processor (5), information labelled with all or some of the diagnosis items (e.g., dry, sensitive, inflammatory, with hair loss, good, oily, scurfy, and seborrhoeic), conduct a specific precision diagnosis by the deep learning algorithm, and derive a final diagnosis result.

The second exemplary embodiment of the present disclosure includes database (4) accumulating therein scalp measurement, diagnosis, and recommendation data, which are provided to the main processor so as to enable learning and interpretation.

Figure 5:
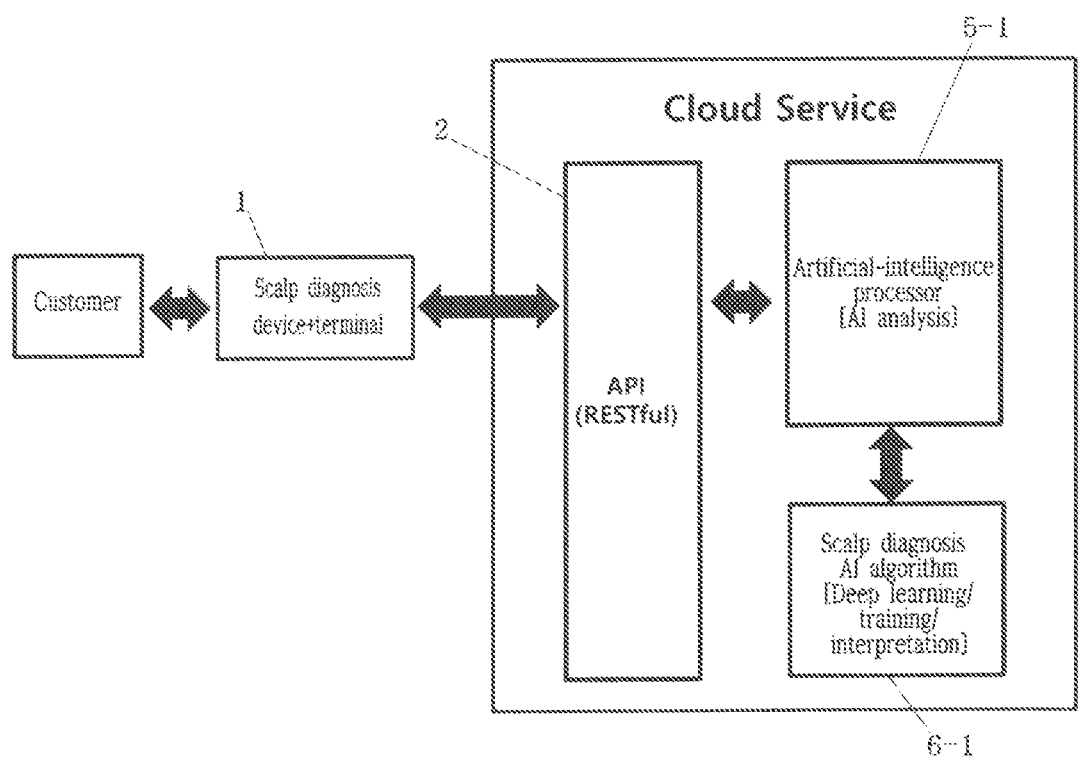
FIGS. 5 and 6 are block diagrams as a whole showing a scalp diagnosis function by an artificial intelligence (deep learning) image analysis as an artificial intelligence-based scalp image diagnostic analysis system using big data, according to the present disclosure.
Figure 6:
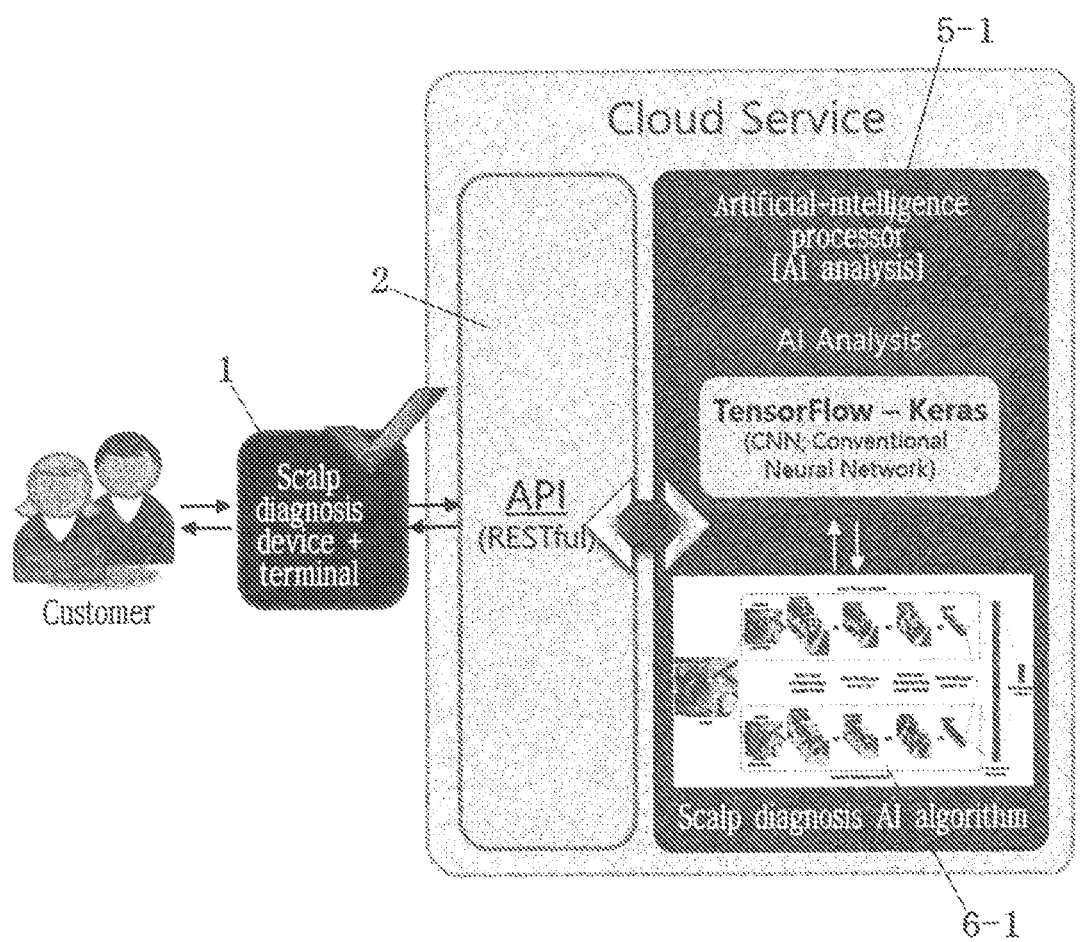

According to the third exemplary embodiment of the present disclosure, as shown in FIGS. 5 and 6, an artificial-intelligence processor (5-1) is configured to receive, from a diagnostician, a scalp image obtained by any one of the scalp diagnosis device and a terminal (1) through API(RESTful) (2) as a cloud service, and perform an AI analysis to label the received scalp image with all or some of the diagnosis items.

The artificial-intelligence processor (5-1) learns about the scalp by utilizing information of big data as a deep learning stage and collects data, and labels the collected learning data, conducts learning and verification to label the collected data with learning data and test data (8:2), and derives an inference model (CNN: Convolutional Neural Network).

The deep learning uses TensorFlow and utilizes an inception V3 model, to label the scalp image with all or some of the diagnosis items by scalp labelling (CNN: object recognition) through retraining.

The third exemplary embodiment of the present disclosure includes a scalp diagnosis AI algorithm (6-1) configured to receive, from the artificial-intelligence processor (5-1), information labelled with all or some of the diagnosis items, conduct a specific precision diagnosis by performing learning and interpretation by use of information of big data by a deep learning algorithm; and derive a final diagnosis result.

The scalp diagnosis AI algorithm (6-1) infers an image from the information labelled with each diagnosis item by additionally retraining a scalp image set by use of the inception V3 model (refer to FIG. 7) as deep learning algorithm, thereby deriving a final diagnosis result with a specific precision diagnosis.

MODE FOR INVENTION

Hereinbelow, exemplary embodiments of the present disclosure will be described in detail with reference to the accompanying drawings.

The terms defined in describing the present disclosure are defined in consideration of functions or configurations in the present disclosure, according to which the terms shall not be understood to have any meaning to limit the technical components of the present disclosure.

The present disclosure may be embodied in many different forms. In this regard, the present disclosure will be described in detail based on aspects (or embodiments). However, the present disclosure should not be construed as being limited to only the embodiments set forth herein, but should be construed as covering modifications, equivalents or alternatives falling within ideas and technical scopes of the present disclosure.

Also, for convenience of understanding of the elements, in the figures, sizes or thicknesses may be exaggerated to be large (or thick), may be expressed to be small (or thin) or may be simplified for clarity of illustration, but due to this, the protective scope of the present disclosure should not be interpreted narrowly.

The terminology used herein is for the purpose of describing particular aspects (or embodiments) only and is not intended to be limiting of the present disclosure.

It will be further understood that such terms that are generally used and defined in dictionaries should be interpreted as having such a meaning that is consistent with their meaning in the context of the relevant art and will not be interpreted in an idealized or overly formal sense unless expressly so defined herein.

Hereinbelow, exemplary embodiments to accomplish the objectives of the present disclosure will be described with reference to the accompanying drawings.

Figure 3:
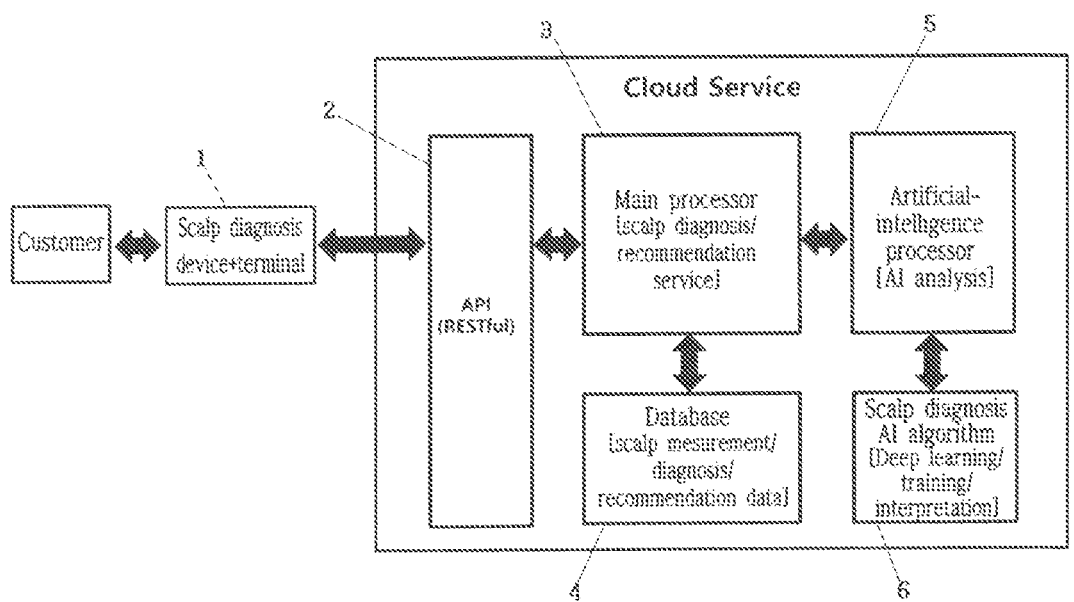
FIGS. 3 and 4 are block diagrams as a whole illustrating a scalp diagnosis function by an artificial intelligence (deep learning image) analysis as an artificial intelligence-based scalp image diagnostic analysis system using big data, and a product recommendation system using the same, according to the present disclosure.
Figure 4:
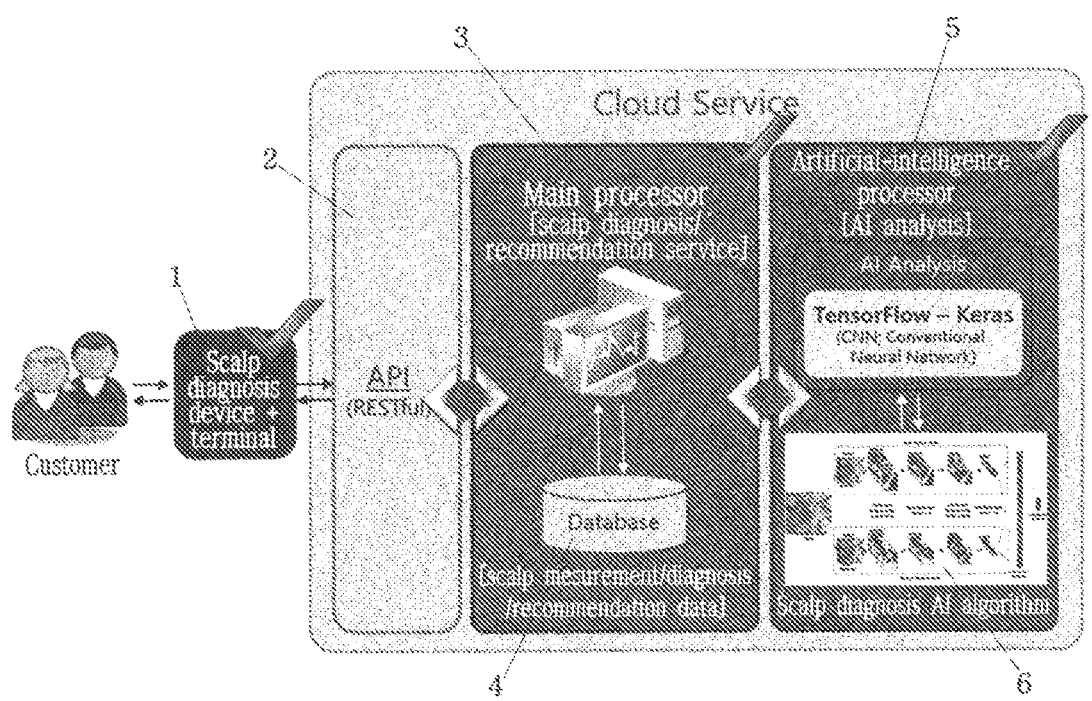

As illustrated in FIGS. 3 and 4, the main processor (3) is configured to receive, from a diagnostician information, about a customer's history taken by the diagnostician by asking about the customer's history, and a scalp image obtained by any one of a scalp diagnosis device and a terminal, through API(RESTful) (2) as a cloud service, perform a diagnosis by a self-diagnosis algorithm with respect to the received history-taking information, and transmit the received scalp image to an to artificial-intelligence processor, for performing scalp diagnosis. The artificial-intelligence processor (5) is configured to perform an AI analysis to label the scalp image received from the main processor with all or some of diagnosis items (e.g., dry, sensitive, inflammatory, with hair loss, good, oily, scurfy, and seborrhoeic) by use of data accumulated in the database (4). The scalp diagnosis AI algorithm (6) is configured to receive, from the artificial-intelligence processor (5), information labeled with all or some of the diagnosis items (e.g., dry, sensitive, inflammatory, with hair loss, good, oily, scurfy, and seborrhoeic), conduct a specific precision diagnosis by performing learning and interpretation by a deep learning algorithm, and derive a final diagnosis result. The database (4) accumulates therein scalp measurement, diagnosis and recommendation data, which are provided to the main processor, to thereby enable self-scalp analysis and recommendation service to be performed.

With respect to the information taken about the customer's history and the scalp image received from the diagnostician, the main processor (3) performs a diagnosis with respect to the history-taking information by a self-diagnosis algorithm constructed in the main processor (3). That is, the main processor (3) receives scalp information data accumulated in the database and diagnoses the customer's history-taking information received from the diagnostician by the self-algorithm.

With respect to the scalp image, the scalp image is labelled with all or some dry, sensitive, inflammatory, with hair loss, good, oily, scurfy, and seborrhoeic by use of the information of big data accumulated in the database and a precision diagnosis is extracted from the labelled information by the scalp diagnosis AI algorithm, and the diagnosis result thereof and a diagnosis based on the history-taking information, are transmitted back to the diagnostician's terminal in real time through API, together with a recommended product as a suitable prescription.

The artificial intelligence processor (5) learns about the scalp with respect to the received scalp image by utilizing information of big data as a deep learning stage and collects data, and labels the collected learning data, conducts learning and verification to label the collected data with learning data and test data (8:2), and derives an inference model (CNN: Convolutional Neural Network).

For example, in a case of using a deep learning model of Google, TensorFlow is used and the Inception V3 model is utilized, and scalp labelling (CNN: object recognition) is performed through retraining, thereby labelling the scalp with all or some of the diagnosis items (dry, sensitive, inflammatory, with hair loss, good, oily, scurfy, and seborrhoeic).

The scalp diagnosis algorithm (6) receives, from the artificial intelligence processor (5), information labelled with all or some of the diagnosis items such as dry, sensitive, inflammatory, with hair loss, good, oily, scurfy, and seborrhoeic, conducts learning and interpretation with respect to the received labelling information by using information of the big data in the database and the Inception V3 model (refer to FIG. 7) as a deep learning algorithm, and inferring an image by additionally retraining a scalp image set, thereby deriving a final diagnosis result with a specific precision diagnosis.

The diagnosis method as described above employs the deep learning model of Google, to which exemplary embodiments of the present disclosure are not limited, and other deep learning models, e.g., by Microsoft, etc. may also be used.

The derived final diagnosis result is transmitted to the main processor (3) through the artificial-intelligence processor (5).

The database (4) accumulates scalp measurement, diagnosis and recommendation dater therein, which are provided to the main processor (3), to enable learning and interpretation.

According to the second exemplary embodiment of the present disclosure, the main processor (3) is configured to receive, from a diagnostician, information about a customer's history taken by the diagnostician by asking about the customer's history, and a scalp image obtained by any one of a scalp diagnosis device and a terminal, through API (RESTful) (2) as a cloud service, conduct a diagnosis by a self-diagnosis algorithm with respect to the received history-taking information; labels the received scalp image by an artificial intelligence (AI) analysis with all or some of the diagnosis items (e.g., dry, sensitive, inflammatory, with hair loss, good, oily, scurfy, and seborrhoeic), by use of information of big data accumulated in database, extracts a precision diagnosis from the labelled information by a scalp diagnosis AI algorithm, and transmit a diagnosis result therefrom and a diagnosis based on the customer's history-taking information in real time back to a terminal of the diagnostician through the API, together with a recommended product customized by suitable prescription.

The artificial-intelligence processor (5) is configured to perform an AI analysis and recommendation service to label the scalp image received from the main processor (3) with all or some of the diagnosis items (e.g., dry, sensitive, inflammatory, with hair loss, good, oily, scurfy, and seborrhoeic), by use of the data accumulated in the database (4).

The scalp diagnosis AI algorithm (6) is configured to receive, from the artificial intelligence processor (5), information labelled with all or some of the diagnosis items (e.g., dry, sensitive, inflammatory, with hair loss, good, oily, scurfy, and seborrhoeic), conduct a specific precision diagnosis by a deep learning algorithm, and derive a final diagnosis result.

The second exemplary embodiment of the present disclosure includes database accumulating therein scalp measurement, diagnosis, and recommendation data, which are provided to the main processor, to thereby enable learning and interpretation.

Figure 8C:
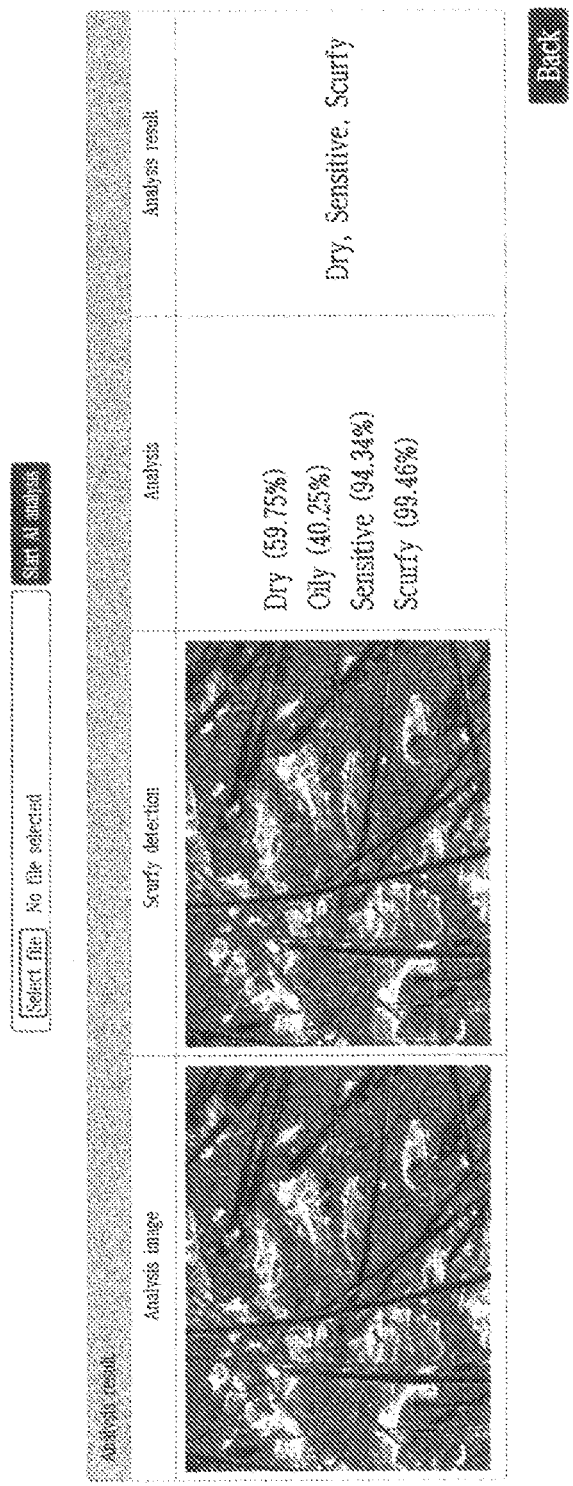

The present disclosure enables a scalp diagnosis by the diagnostician to be accurate and also the diagnosis result to be promptly obtained in real time, through history taking associated with the customer's scalp and a scalp image analysis, as shown in FIGS. 8a, 8b, and 8c.

That is, if a diagnostician (user) inputs history-taking information associated with the customer's scalp and a scalp image by means of a terminal, it is possible to immediately obtain the final analysis result in real time through an AI analysis as described above in detail.

Upon obtaining the final analysis result about the customer's scalp according to the AI analysis, the customer can receive the prescription and a product recommended by the diagnostician (user), which is customized according to the final analysis result.

That is, the customer can receive the customized product from the diagnostician (user) by a variety of algorithms according to the final analysis result associated with the customer's scalp.

For example, products recommended on the basis of the scalp diagnosis result are shampoo and scalp serum, and product division and algorithm are as shown in FIG. 9.

TABLE 1

Algorithm technique to label the scalp for scalp care customized for each customer through product recommendation by an artificial intelligence analysis/diagnosis with respect to images of scalp measurement by a diagnostician

| Scalp type A<br>Itchy and oily scalp | Scalp type B<br>Dry and flaky scalp | Scalp type C<br>Troubled (eruption, etc.) scalp |
| --- | --- | --- |
| A-1. Scalp having active secretion of sebum | B-1. Dry scalp | |
| A-2. Scalp having active secretion of sebum and accompanying inflammation | B-2. Dry scalp having dead skin cells flying like powder | C-1. Scalp soothing and post-treatment |
| A-3. Seborrhoeic scalp | A-3. Atopic scalp | C-2. Papular and pustular due to folliculitis |
| Scalp Type D<br>Sensitive scalp | Scalp Type E<br>Folliculitis scalp | Scalp Type F<br>Good scalp |

FIG. 10 shows the first determination of scalp type according to a customer's history taking, the second determination of divided scalp type through a scalp image artificial intelligence analysis and diagnosis, and algorithm/system.

TABLE 2

11 kinds of scalp shampoos and 12 kinds of customized scalp serums available for customized recommendation according to the customer's divided scalp type are defined and determined.

| Customized shampoo based on scalp diagnosis result: | 11 kinds |
| --- | --- |
| Customized serum based on scalp diagnosis result: | 12 kinds |

FIG. 11 shows determination of mapping algorithm and system for scalp care shampoo and serum products customized according to the determination of scalp type through by the scalp image artificial-intelligence analysis and diagnosis.

FIG. 12 shows an algorithm and a system for product recommendation conducted by defining customized scalp care shampoo and serum respectively, through division of recommended products according to the result of an artificial intelligence diagnosis by a diagnostician.

As a third exemplary embodiment of the present disclosure, an artificial-intelligence processor (5-1) is configured to receive, from the diagnostician, a scalp image acquired by any one of the scalp diagnosis device or the terminal (1) through API(RESTful) (2) as a cloud service, and performs an AI analysis with respect to the received scalp image to label the scalp image with all or some of the diagnosis items, as illustrated in FIGS. 5 and 6.

The artificial-intelligence processor (5-1) learns about the scalp by utilizing information of big data as a deep learning stage and collects data, and labels the collected learning data, conducts learning and verification to label the collected data with learning data and test data (8:2), and derives an inference model (CNN: Convolutional Neural Network).

The deep learning uses TensorFlow and utilizes an inception V3 model, to label the scalp image with all or some of the diagnosis items by scalp labelling (CNN: object recognition) through retraining.

The third exemplary embodiment of the present disclosure includes the scalp diagnosis AI algorithm (6-1) configured to receive, from the artificial-intelligence processor (5-1), information labelled with all or some of the diagnosis items, conduct a specific precision diagnosis by performing learning and interpretation by use of information of big data by a deep learning algorithm; and derive a final diagnosis result.

The scalp diagnosis AI algorithm (6-1) infers an image from the information labelled with each diagnosis item by additionally retraining a scalp image set by use of the inception V3 model (refer to FIG. 7) as deep learning algorithm, thereby deriving a final diagnosis result with a specific precision diagnosis.

The above-described diagnosis method uses a deep learning model of Google, to which exemplary embodiments of the present disclosure are not limited, and other deep learning models, e.g., by Microsoft, etc. may also be used.

All or some of the diagnosis items as described above refer to all or some of dry, sensitive, inflammatory, with hair loss, good, oily, scurfy, and seborrhoeic.

According to the present disclosure as described above, an accurate analysis diagnosis function through an artificial intelligence (deep learning) image analysis with the scalp image measured by a diagnostician is realized, a diagnosis result can be confirmed in real time, the diagnosis result with higher accuracy can be obtained, and also a product suitable for a customer's scalp status can be recommended according to the result of diagnosis by artificial intelligence.

INDUSTRIAL APPLICABILITY

According to the present disclosure, an accurate diagnosis function through an artificial intelligence (deep learning) image analysis using a scalp image measured by a diagnostician can be achieved, and a product that is suitable for the state of the scalp according to the diagnosis result diagnosed by means of artificial intelligence can be recommended

The invention claimed is:

1. An artificial intelligence-based scalp image diagnostic analysis system using big data, the system comprising:
 a main processor (3) configured to: receive, from a diagnostician, information about a customer's history taken by the diagnostician by asking about the customer's history, and a scalp image obtained by any one of a scalp diagnosis device and a terminal, through API (RESTful) (2) as a cloud service; conduct a diagnosis by a self-diagnosis algorithm with respect to the received history-taking information; and transmit the received scalp image to an artificial-intelligence processor (5), for performing a scalp diagnosis;
 the artificial-intelligence processor (5) configured to perform an artificial intelligence (AI) analysis to label the scalp image received from the main processor (3) with all or some of diagnosis items by use of data accumulated in database (4);

wherein the artificial-intelligence processor (5) learns about the scalp by the artificial intelligence (AI) analysis using information of big data and collect learning data as a deep learning stage, labels the collected learning data, conducts learning and verification to label the collected data with learning data and test data, and derives an inference model (CNN: Convolutional Neural Network), wherein the deep learning conducts scalp labelling (CNN: object recognition) through retraining by use of TensorFlow and an Inception V3 model, whereby the scalp is labelled with all or some of the diagnosis items, a scalp diagnosis AI algorithm (6) configured to: receive, from the artificial-intelligence processor (5), information labeled with all or some of the diagnosis items; conduct a specific precision diagnosis by performing learning and interpretation by a deep learning algorithm, and derive a final diagnosis result; and the database (4) accumulating therein scalp measurement, diagnosis, and recommendation data, which are provided to the main processor, thereby enabling self-scalp a diagnosis and recommendation service to be performed, wherein the artificial-intelligence processor counts multiple numbers of hair follicle groups and multiple number of follicles within each group based on a microscopic image of a sample from a human scalp, and wherein the diagnosis items include the scalp types which are dry, sensitive, inflammatory, with hair loss, good, oily, scurfy, and seborrhoeic.

2. The system of claim 1, wherein the scalp diagnosis AI algorithm (6) infers an image through additional retraining from a scalp image set drawn by use of the inception V3 model as the deep learning algorithm, and derives a final diagnosis result through a precision diagnosis based on information labelled with each diagnosis item.

3. An artificial intelligence-based scalp image diagnostic analysis system using big data, the system comprising:

a main processor (3) configured to: receive, from a diagnostician, information about a customer's history taken by the diagnostician by asking about the customer's history, and a scalp image obtained by any one of a scalp diagnosis device and a terminal (1), through API (RESTful) (2) as a cloud service; conduct a diagnosis by a self-diagnosis algorithm with respect to the received information; label the received scalp image by an artificial intelligence (AI) analysis with all or some of diagnosis items by use of information of big data accumulated in database; extract a precision diagnosis from the labelled information by a scalp diagnosis AI algorithm; and transmit a diagnosis result therefrom and a diagnosis based on the information taken about the customer's history in real time back to a terminal of the diagnostician through the API, together with a recommended product customized by suitable prescription;

the artificial-intelligence processor (5) configured to perform an AI analysis and recommendation service to label the scalp image received from the main processor (3) with all or some of diagnosis items by use of the data accumulated in the database (4);

wherein the artificial-intelligence processor (5) learns about the scalp by the artificial intelligence (AI) analysis using information of big data and collect learning data as a deep learning stage, labels the collected learning data, conducts learning and verification to label the collected data with learning data and test data, and derives an inference model (CNN: Convolutional Neural Network), wherein the deep learning conducts scalp labelling (CNN: object recognition) through retraining by use of TensorFlow and an Inception V3 model, whereby the scalp is labelled with all or some of the diagnosis items, a scalp diagnosis AI algorithm (6) configured to: receive, from the artificial-intelligence processor (5), information labeled with all or some of the diagnosis items; conduct a specific precision diagnosis by a deep learning algorithm, and derive a final diagnosis result; and the database (4) accumulating therein scalp measurement, diagnosis, and recommendation data, which are provided to the main processor, thereby enabling learning and interpretation, wherein the artificial-intelligence processor counts multiple numbers of hair follicle groups and multiple number of follicles within each group based on a microscopic image of a sample from a human scalp, and wherein the diagnosis items include the scalp types which are dry, sensitive, inflammatory, with hair loss, good, oily, scurfy, and seborrhoeic.

4. The system of claim 3, wherein the customer receives recommendation by the diagnostician (user) of a product customized for the customer by various algorithms according to the final analysis result about the customer's scalp.

5. An artificial intelligence-based scalp image diagnostic analysis system using big data, the system comprising:

an artificial-intelligence processor (5-1) configured to: receive, from a diagnostician, a scalp image obtained by any one of a scalp diagnosis device and a terminal, through API (RESTful) (2) as a cloud service; and perform an artificial intelligence (AI) analysis with respect to the received history-taking information to label the received information with all or some of diagnosis items;

wherein the artificial-intelligence processor (5-1) learns about the scalp by the artificial intelligence (AI) analysis using information of big data and collect learning data as a deep learning stage, labels the collected learning data, conducts learning and verification to label the collected data with learning data and test data, and derives an inference model (CNN: Convolutional Neural Network), wherein the deep learning conducts scalp labelling (CNN: object recognition) through retraining by use of TensorFlow and an Inception V3 model, whereby the scalp is labelled with all or some of the diagnosis items, a scalp diagnosis AI algorithm (6-1) configured to: receive, from the artificial-intelligence processor (5-1), information labeled with all or some of the diagnosis items; conduct a specific precision diagnosis by performing learning and interpretation by use of information of big data by a deep learning algorithm; and derive a final diagnosis result, wherein the artificial-intelligence processor counts multiple numbers of hair follicle groups and multiple number of follicles within each group based on a microscopic image of a sample from a human scalp, and wherein the diagnosis items include the scalp types which are dry, sensitive, inflammatory, with hair loss, good, oily, scurfy, and seborrhoeic.

6. The system of claim 5, wherein the scalp diagnosis AI algorithm (6-1) infers an image by additional retraining a scalp image set drawn by use of the inception V3 model as the deep learning algorithm, and derives a final diagnosis result through a precision diagnosis based on information labelled with each diagnosis item.

\* \* \* \* \*